United States Patent
Ruecroft et al.

(10) Patent No.: US 9,278,323 B2
(45) Date of Patent: Mar. 8, 2016

(54) PROCESS FOR MAKING CRYSTALS

(75) Inventors: Graham Ruecroft, Oxford (GB); James Robinson, Oxford (GB); Dipesh Parikh, Oxford (GB)

(73) Assignee: Prosonix Limited (GB)

( * ) Notice: Subject to any disclaimer, the term of this patent is extended or adjusted under 35 U.S.C. 154(b) by 431 days.

(21) Appl. No.: 12/665,019

(22) PCT Filed: Jun. 17, 2008

(86) PCT No.: PCT/GB2008/050452
§ 371 (c)(1),
(2), (4) Date: Dec. 16, 2009

(87) PCT Pub. No.: WO2008/155570
PCT Pub. Date: Dec. 24, 2008

(65) Prior Publication Data
US 2010/0190760 A1 Jul. 29, 2010

(30) Foreign Application Priority Data
Jun. 18, 2007 (GB) .................................. 0711680.9

(51) Int. Cl.
*B01J 19/10* (2006.01)
*B01J 2/06* (2006.01)
(Continued)

(52) U.S. Cl.
CPC ... *B01J 2/06* (2013.01); *A61K 9/14* (2013.01); *B01D 9/0009* (2013.01); *B01D 9/0054* (2013.01); *B01D 9/0081* (2013.01); *B01J 2/18* (2013.01); *A61K 9/0073* (2013.01)

(58) Field of Classification Search
CPC ............ B01J 2/06; B01J 2/18; B01D 9/0081; B01D 9/0009; B01D 9/0054; A61K 9/14; A61K 9/0073
USPC ........................... 204/157.62, 157.42, 165.62
See application file for complete search history.

(56) References Cited

U.S. PATENT DOCUMENTS 4,023,935 A   5/1977 Levinthal et al.
5,874,029 A * 2/1999 Subramaniam et al. ........ 264/12
(Continued)

FOREIGN PATENT DOCUMENTS

EP         1688169       8/2006
WO      WO9952507      10/1999
(Continued)

OTHER PUBLICATIONS

PCT International Search Report and Written Opinion for International Application No. PCT/GB2008/050452 dated Oct. 6, 2008.
(Continued)

*Primary Examiner* — Keith Hendricks
*Assistant Examiner* — Colleen M Raphael
(74) *Attorney, Agent, or Firm* — Tumey L.L.P.

(57) ABSTRACT

A process for preparing an emulsion or a dispersion comprising crystalline particles of at least one active principal that comprises contacting a solution of at least one solute in a solvent or mixture of solvents in a first flowing stream with a non-solvent in a second flowing stream wherein the non-solvent and solvent are not miscible with each other, so as to form an emulsion or a dispersion. Super saturation is brought about by suitable means, and the emulsion or dispersion is subjected to ultrasonic irradiation to mediate crystal nucleation.

10 Claims, 3 Drawing Sheets

(51) Int. Cl.
*A61K 9/14* (2006.01)
*B01D 9/00* (2006.01)
*A61K 9/00* (2006.01)
*B01J 2/18* (2006.01)

(56) References Cited

U.S. PATENT DOCUMENTS

| | | | |
|---|---|---|---|
| 6,482,438 | B1 | 11/2002 | Singh et al. |
| 6,517,853 | B1 | 2/2003 | George et al. |
| 6,960,256 | B2 * | 11/2005 | Bowe et al. ............... 422/245.1 |
| 7,208,106 | B2 * | 4/2007 | Shekunov et al. ............... 264/5 |
| 2003/0181432 | A1 * | 9/2003 | Lancaster et al. ............ 514/175 |
| 2004/0045805 | A1 * | 3/2004 | Lancaster et al. ........ 204/157.43 |
| 2004/0091407 | A1 * | 5/2004 | Lancaster et al. .......... 422/245.1 |
| 2004/0197275 | A1 * | 10/2004 | Jongen et al. .................... 424/46 |
| 2004/0256749 | A1 * | 12/2004 | Chaubal et al. .................... 264/5 |
| 2004/0258756 | A1 * | 12/2004 | McLoughlin ................ 424/489 |
| 2006/0096522 | A1 | 5/2006 | Singh |
| 2006/0182808 | A1 * | 8/2006 | Bakker et al. ................. 424/489 |
| 2006/0255323 | A1 * | 11/2006 | Seki et al. ................. 252/519.21 |
| 2007/0065372 | A1 * | 3/2007 | Price et al. .................... 977/906 |

FOREIGN PATENT DOCUMENTS

| | | |
|---|---|---|
| WO | WO0032597 | 6/2000 |
| WO | WO0038811 | 7/2000 |
| WO | WO03061816 | 7/2003 |
| WO | WO 03061816 A1 * | 7/2003 |
| WO | WO2004004862 | 1/2004 |

OTHER PUBLICATIONS

UK Search Report for Application No. GB0811007.4 dated Oct. 15, 2008.
USPTO Office Action for U.S. Appl. No. 12/531,322 dated Jul. 11, 2011.
USPTO Office Action for U.S. Appl. No. 12/531,322 dated Jan. 18, 2012.
Almeida; Amaral; Lobao, "Comparative study of sustained-release lipid microparticles and solid dispersions containing ibuprofen", Brazilian Journal of Pharmaceutical Sciences, vol. 48, n. 3, Jul./Sep. 2012.
Martin; Cains; Price, "Sonochemistry", FCW pp. 6-9, Dec. 1997.
Martin, "The Third International Conference on the Scale-Up of Chemical Processes", Conference Proceedings, Sep. 21-24, 1998.
Martin; Ward, "Reactor Design for Sonochemical Engineering", Trans IChemE, vol. 70, Part A, May 1992.
Canadian Office Action for Canadian Application No. 2,680,105 dated Nov. 1, 2013.

* cited by examiner

Figure 3:
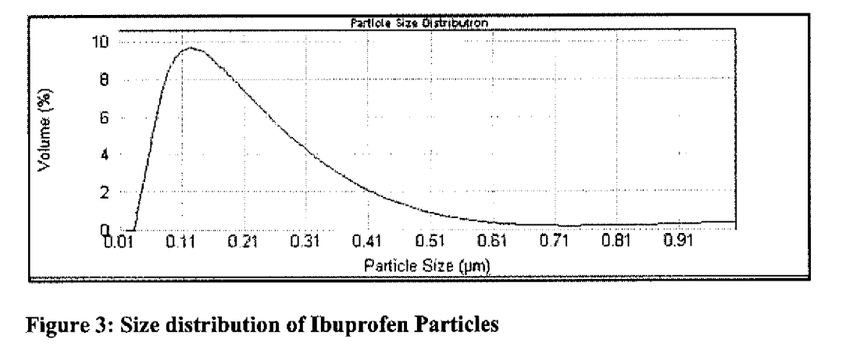

Figure 3: Size distribution of Ibuprofen Particles

Figure 4:
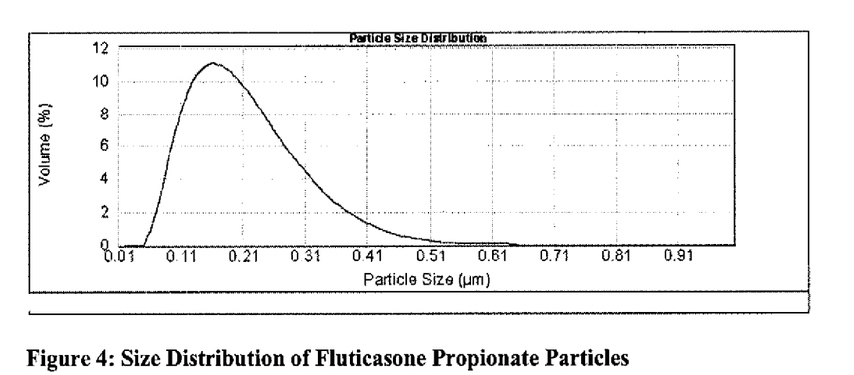

Figure 4: Size Distribution of Fluticasone Propionate Particles

Figure 5:
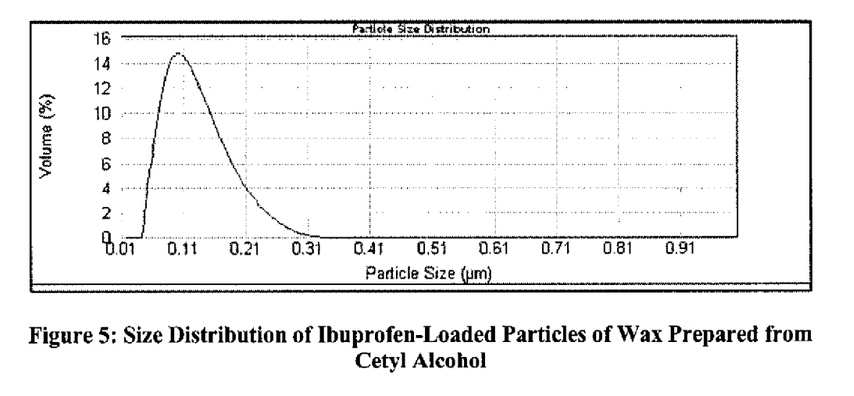
Figure 6:
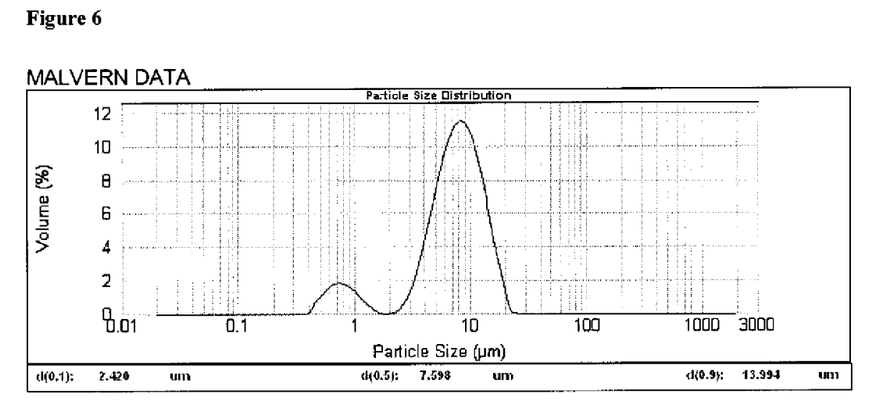
Figure 7:
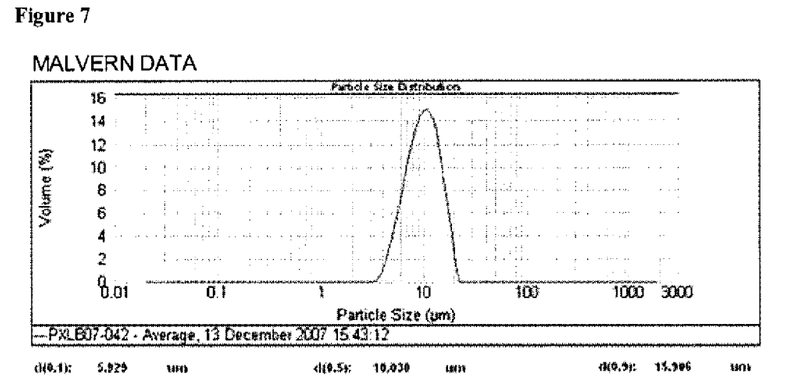

Figure 5: Size Distribution of Ibuprofen-Loaded Particles of Wax Prepared from Cetyl Alcohol

PROCESS FOR MAKING CRYSTALS

FIELD OF THE INVENTION

This invention relates to a process for preparing small crystals in the presence of ultrasonic irradiation wherein at least two different liquids are employed.

BACKGROUND OF THE INVENTION

The control of crystal and precipitate particle size is very important in some circumstances, in particular in the pharmaceutical and agro-chemical industries in which the final product form of the active principal of interest is in the form of a fine powder. The manner in which an active principal behaves in a biological system depends upon many factors inter alia the size of the particle and the crystal form. Small particles may be made by processes such as milling, but such processes may have a detrimental effect on the material properties and may also produce a significant proportion of particles which are unsuitable for the desired use, for example, they may be of an inappropriate shape. Such particles may undergo morphological alterations, leading to undesirable surface polymorphological transformation which in turn may give rise to the formation of amorphous structures. The particles may become highly charged which may contribute to undermining flow-rates. Also, particles destined for use in aerosols may be compromised should they become highly charged. Crystallisation of crystals in the desired size range directly from solution would be desirable.

For many years it has been known to bring about crystallisation by mixing a solvent containing an active principal to be crystallised with an anti-solvent, so that after mixing the solution is supersaturated and crystallisation occurs. The mixing may occur in the presence of ultrasonic irradiation or in a different manner in which ultrasonic irradiation is not used eg fluidic vortex mixing. The term "anti-solvent" means a fluid which promotes precipitation from the solvent of the active principal of interest (or of a precursor of the active principal). The anti-solvent may comprise a cold gas, or a fluid which promotes the precipitation via a chemical reaction, or which decreases the solubility of the active principal of interest in the solvent; it may the same liquid as the solvent but at a different temperature, or it may be a different liquid from the solvent.

EP 1144065 describes a system in which mixing of anti-solvent with solvent comprising an active principal to be crystallised is achieved by using a flow rate ratio of anti-solvent:solvent of up to 10:1 in the presence of ultrasonic irradiation in a continuous flow cell. It is described that a warm solvent is mixed with a cold miscible anti-solvent, although the actual temperature of the cold anti-solvent is not disclosed.

EP 1469938 describes a system in which the flow rate of mixing of anti-solvent with solvent comprising an active principal to be crystallised exceeds that of the solvent, at a flow rate ratio of up to 10:1, typically of from 2:1 up to 5:1. The mixing is carried out in the presence of ultrasonic radiation.

The prior art processes enable the production of crystals using flow rate ratios of anti-solvent: solvent that are generally lower than 20:1 (i.e. towards a flow rate ratio of 10:1 to as low as 1:1).

SUMMARY OF THE INVENTION

According to the present invention there is provided a process for preparing an emulsion or a dispersion comprising crystalline particles of at least one active principal that comprises contacting a saturated solution of at least one solute in a solvent in a first flowing stream with a non-solvent in a second flowing stream wherein the non-solvent and solvent are not miscible with each other, forming an emulsion or a dispersion wherein the said solute is present in a super-saturated solution within the droplets of the emulsion or dispersion so formed, and subjecting the emulsion or dispersion to ultrasonic irradiation.

Preferably, the non-solvent stream and solvent stream flow at a flow rate ratio of greater than 20:1.

The non-solvent stream may be re-circulated, for example, in a continuously re-circulating flowing stream, that is to say, a second flowing stream. Typically, there is provided a process according to the invention wherein the second flowing stream is a continuously recycling non-solvent stream that can also comprise added solute in solvent, wherein the flow rate ratio of the said second flowing stream (i.e. being or comprising non-solvent): the first flowing stream (i.e. being or comprising solvent) can be any flow rate ratio depending on design and the end purpose for the crystals that are obtained using the process of the invention. The flow rate ratio employed in the process of the invention may be decided taking into account the substance of interest, the desired size of the crystals required for a given purpose, and how the crystals are to be administered to a subject, such as to a mammal (e.g. a human being; a horse; a bovine animal; a pig; or a sheep) in the form of a suitable medicament, or to a plant in the form of a suitable agrochemical, for example a pesticide, a herbicide, a fungicide, bactericide, or a virucide. Suitable flow rate ratios for use in the process of the invention may be any flow rate ratio of the second flowing stream:first flowing stream, up to 1000:1, for example, 900:1, 800:1, 700:1, 600:1, 500:1, 400:1, 300:1, 200:1, 100:1, 50:1, 40:1, 30:1 or 20:1, 10:1, 5:1, 4:1, 3:1, 2:1 or 1:1 or any flow rate ratio there between, such as 380:1, 330:1, 333:1, 165:1, 80:1, 60:1, 40:1, 30:1, 20:1 and the like. Preferred flow rate ratios include from at least 20:1 up to 1000:1; from at least 20:1 up to 800:1; from at least 20:1 up to 600:1. The flow rate ratio will be governed by the size of the crystals that are required for a given end purpose and the proposed delivery vehicle for them that is to be used in a subject organism.

Emulsions and dispersions and their formation are well-known in the art. Emulsions are, by definition, droplets that are stabilised in a continuous phase, for example through the use of surfactants known in the art. Dispersions can be viewed as droplets dispersed in a continuous phase wherein the droplets are not stabilised, that is to say, they do not remain as droplets but after a short time coalesce forming a two phase system with the continuous phase. In order to stabilise dispersions, it is known in the art to add surfactants or other stabilising agents to them, enabling the formation of stabilised droplets and thereby, a stable emulsion.

The droplets may be of an organic or inorganic liquid, and the continuous phase may be aqueous or non-aqueous depending on end purpose and design. Typically, emulsions of the present invention comprise droplets of an organic liquid comprising solute (i.e. made up of at least one active principal), and the continuous phase is an aqueous phase, together forming an aqueous dispersion or emulsion.

The emulsion may optionally contain additives such as surfactants and dispersants, known in the art, for assisting the formation and stabilization of the emulsion. Such surfactants and dispersants will be chosen according to the nature of the emulsion, and may be non-ionic, anionic and/or cationic depending on design. Additives will normally be present in an amount of 0.01-30 w/w %, preferably 0.1-20 w/w %.

The droplets typically vary in diameter from approximately 0.05 to 80 µm. Droplets with diameter in the range of 0.3 to 80 µm are known as "macro-droplets", and the emulsions as "macro-emulsions". Droplets with diameter in the range of 0.05 to 0.3 µm are known as "micro-droplets", and the emulsions as "micro-emulsions". For the purposes of the present invention, the terms "droplets" and "emulsions" as used herein encompass both macro- and micro-droplets and macro- and micro-emulsions.

The organic liquid phase of the droplet will be water insoluble. 'Water insoluble' in this context means anything less than fully water miscible, preferably water immiscible, though in some situations, the organic liquid phase will dissolve in water typically in an amount of not more than 10% w/w at a temperature at which crystallisation can take place.

The emulsion may further contain a buffering agent, such as sodium acetate and acetic acid, for maintaining the pH of the emulsion at a desired level, anti-freeze agents and solubility adjusting agents, as is known in the art; and may also contain a solubilizer for an active principal or principals, such as acetone or dichloromethane or a mixture of cetyl alcohol and dichloromethane, which can be easily removed following crystallisation and re-used.

Formation of the original emulsion may be carried out in the vessel in which crystallisation takes place, or can be carried out in a separate vessel which is preferably equipped with means for high flow throughput of the non-solvent or it may be equipped with mixing, high shear equipment and/or heating means such that an optimum emulsion can be produced. To ensure the solution (and so the emulsified droplets) becomes supersaturated, the solution prior to forming an emulsion is prepared in a saturated state either
(i) at a temperature which is higher or lower than the temperature of the non-solvent (for example 1-20° C. higher, or lower, if the solubility decreases with temperature, for example from 1-20° C. lower) and thereby generating super-saturation when it is contacted with the cooler or warmer non-solvent;
(ii) at a warmer temperature to the non-solvent where the solvent is volatile at the temperature of the non-solvent thus leading to evaporation from the emulsified droplet and hence super-saturation occurs within the emulsified droplet; or
(iii) at a warmer or similar temperature to the non-solvent when the initial solution also comprises a miscible co-solvent at a temperature above the melting point of the solute, thereby generating emulsified melt droplets as the miscible co-solvent disperses into the non-solvent.

In each case as super-saturation is generated, ultrasound mediates nucleation that leads to the formation of crystals.

Isolation of crystals from the emulsion can be carried out by any conventional means, such as by filtration, centrifugation, spray-drying, supercritical carbon dioxide evaporation or evaporation. Typically, crystals are isolated by evaporative methods.

By manipulating the flow rate ratio of non-solvent to solvent in the process of the present invention the inventors have now made it possible to provide crystals of active principals of interest of a desired size of up to about 10 µm in size. The mean diameter size of particles that are able to be attained using the method of the invention lies in the range of from 100 nm up to 10 µm, preferably from about 100 nm to about 5 µm and most preferably from 100 nm to about 2 µm, for example, 100 nm, 700 nm or 1 µm.

The solute is typically an active principal or a desired precursor thereof, such as a drug or an agro-chemical of interest that is able to form crystals in the process of the invention. There may be more than one solute comprised in the first flowing stream, for example, a mixture of two or more solutes of interest, such as two or more active principals of interest, for example, two or more drugs or two or more agro-chemicals, depending on the proposed end use of the said solutes. Suitable solutes that are able to crystallise under the process conditions of the invention include active principals or drugs which can be formed into crystalline particles by the process of the present invention such as corticosteroids, b2-agonists, anticholinergics, leukotriene antagonists, inhalable proteins or peptides, mometasone furoate; beclomethasone dipropionate; budesonide; fluticasone; dexamethasone; flunisolide; triamcinolone; salbutamol; albuterol; terbutaline; salmeterol; bitolterol; ipratropium bromide; oxitropium bromide; sodium cromoglycate; nedocromil sodium; zafirlukast; pranlukast; formoterol; eformoterol; bambuterol; fenoterol; clenbuterol; procaterol; broxaterol; (22R)-6a,9a-difluoro-11b,21-dihydroxy-16a,17a-propylmethylenedioxy-4-pregnen-3,20-dione; TA-2005; tipredane; insulin; interferons; calcitonins; parathyroid hormones; and granulocyte colony-stimulating factor.

Other particles which may be made according to the invention include any drugs or active principals usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonideor fluticasonei antitussives, e.g. noscapine; bronchodilators, e.g. ephedrine, adrenaline, fenoterol, formoterol, isoprenaline, metaproterenol, phenylephrine, phenylpropanolamime, pirbuterol, reproterol, rimiterol, salbutamol, salmeterol, terbutalin; isoetharine, tulobuterol, orciprenaline or (–)-4-amino-3,5-dichloro-a[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. 25 aminophylline, choline theophyllinate, lysine theophyllinate or theophylline; and therapeutic proteins and peptides, e.g. insulin or glucagon. It will be appreciated by the person skilled in the art that, where appropriate, medicaments comprising active principals or drugs may be used in the form of salts (e.g. as alkali metal or amine salts or as acid addition salts) or as esters (e.g. lower alkyl esters) or as solvates (e.g. hydrates) to optimise the activity and/or stability of the medicament.

Particularly suitable medicaments for preparation with particles obtained in accordance with the process of the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or as the sulphate salt), salmeterol (e.g. as the xinafoate salt), terbutaline (e.g. as the sulphate salt), reproterol (e.g. as the hydrochloride salt), beclomethasone dipropionate (e.g. as the monohydrate), fluticasone propionate or (–)-4-amino-3,5-dichloro-.alpha.-[[[6-[2-(2-pyridinyl) ethoxy]hexyl]amino]-methyl]benzenemethanol and physiologically acceptable salts and solvates thereof.

It will be appreciated by the man skilled in the art that particles made by the process of the invention may contain a combination of two or more active principals. Active principals may be selected from suitable combinations of the active principals mentioned hereinbefore. Thus, suitable combinations of bronchodilatory agents include ephedrine and theophylline, fenoterol and ipratropium, and isoetharine and phenylephrine.

Further suitable combinations of particles of active principals made according to the process of the invention include combinations of corticosteroids, such as budesonide, beclomethasone dipropionate and fluticasone propionate, with b2-agonists, such as salbutamol, terbutaline, salmeterol and formoterol and physiologically acceptable derivatives thereof especially salts including sulphates.

Other examples of particles obtainable by the process of the invention may include a cromone which may be sodium cromoglycate or nedocromil, or a carbohydrate, for example, heparin.

The particles made by the process of the invention may comprise an active principal suitable for inhalation and may be a pharmacologically active agent for systemic use. For example, such active particles may comprise peptides or polypeptides or proteins such as DNase, leukotines or insulin (including pro-insulins), cyclosporin, interleukins, cytokines, anticytokines and cytokine receptors, vaccines, growth hormone, leuprolide and related analogues, interferons, desmopressin, immunoglobulins, erythropoietin and calcitonin.

Alternatively, the active principal made by the process of the invention may be suitable for oral administration. A drug for oral administration may be one of the systemic drugs mentioned above. The active principal may be a substance which exhibits low solubility in the digestive tract, for example, magnesium trisilicate, calcium carbonate and bismuth subnitrate. Organic compounds may include, for example, all products of combinatorial chemistry, rosiglitazone and other related glitazone drugs, hydrochlorothiazide, griseofulvin, lamivudine and other nuclease reverse transcriptase inhibitors, simvastatin and other statin drugs, benzafibrate and other fibrate drugs and loratidine, and any other physiologically tolerable salts and derivatives thereof.

Pharmaceutical excipients suitable for adding to particles made according to the process of the invention include, for example, carbohydrates especially monosaccharides such as fructose, glucose and galactose; non-reducing disaccharides such as sucrose, lactose and trehalose; non-reducing oligosaccharides such as raffinose and melezitose; non reducing starch derived polysaccharides products such as maltodextrins, dextrans and cyclodextrins; and non-reducing alditols such as mannitol and xylitol.

Where the particles of active principal(s) prepared by the process of the present invention are agro-chemically active, the active principal may for example be a plant growth regulator, herbicide, and/or pesticide, for example insecticide, fungicide, acaricide, nematocide, miticide, rodenticide, bactericide, molluscicide or bird repellant.

Examples of organic water-insoluble agrochemical active principals made according to the process of the invention include insecticides, for example selected from the group consisting of carbamates, such as methomyl, carbaryl, carbofuran, or aldicarb; organo thiophosphates such as EPN, isofenphos, isoxathion, chlorpyrifos, or chlormephos; organo phosphates such as terbufos, monocrotophos, or terachlorvinphos; perchlorinated organics such as methoxychlor; synthetic pyrethroids such as fenvalerate; nematicide carbamates, such as oxamyl herbicides, for example selected from the group consisting of triazines such as metribuzin, hexaxinone, or atrazine; sulfonylureas such as 2-chloro-N-[(4-methoxy-6-methyl-1,3,5-triazin-2-yl)aminocarbonyl]-benzenesulfonamide; uracils (pyrimidines) such as lenacil, bromacil, or terbacil; ureas such as linuron, diuron, siduron, or neburon; acetanilides such as alachlor, or metolachlor; thiocarbamates such as benthiocarb (SATURN), triallate; oxadiazol-ones such as oxadiazon; phenoxyacetic acids such as 2,4-D; diphenyl ethers such as fluazifop-butyl, acifluorfen, bifenox, or oxyfluorfen; dinitro anilines such as trifluralin; glycine phosphonates such as glyphosate salts and esters; dihalobenzonitriles such as bromoxynil, or ioxynil; fungicides, for example selected from the group consisting of nitrilo oximes such as cymoxanil (curzate); imidazoles such as benomyl, carbendazim, or thiophanate-methyl; triazoles such as triadimefon; sulfenamides such as captan; dithiocarbamates such as maneb, mancozeb, or thiram; chloronated aromatics such as chloroneb; dichloro anilines such as iprodione; aphicides, for example selected in the group consisting of carbamates, such as pirimicarb; miticides, for example selected from the group consisting of propynyl sulfites such as propargite; triazapentadienes such as amitraz; chlorinated aromatics such as chlorobenzilate, or tetradifan; and dinitrophenols such as binapacryl.

The organic water-insoluble agrochemical active principals may be comprised in the particles produced according to the present invention as a mixture of several ingredients. Especially preferred organic water-insoluble agrochemical active ingredients are atrazine, cymoxanil, chlorothalanil, cyproconazole, and tebuconazole.

The flowing stream of solvent comprising solute or solutes (i.e. the 'solution') and the flowing stream of non-solvent may be contacted or mixed together such that the two streams flow along a single path or axis in the same direction, for example, within the lumen of a suitable delivery means and into a suitable receptacle or chamber, such as an ultrasonic continuous flow cell. Each of the said flowing streams may be pumped at a pre-determined rate of flow from an initial source reservoir into the delivery means. A suitable delivery means may comprise a tubular means such as a straight or curved conduit, for example a pipe, and the two streams may be mixed coaxially therein. Alternatively, the two streams may be introduced into a receptacle or chamber, such as an ultrasonic continuous flow cell, via pumping through separate delivery means, such as two separate tubular means, for example, two pipes.

The flow rate ratio of non-solvent:solvent (the "flow rate ratio" hereinafter) of the invention may be of any flow rate ratio as described herein depending on design and the end purpose for the crystals that are obtained using the process of the invention. The flow rate ratio employed in the process of the invention may be decided taking into account the substance of interest, the desired size of the crystals required for a given purpose, and how the crystals are to be administered to a subject, such as to a mammal (e.g. a human being; a horse; a bovine animal; a pig; or a sheep) in the form of a suitable medicament, or to a plant in the form of a suitable agrochemical, for example a pesticide, a herbicide, a fungicide, bactericide, or a virucide. Suitable flow rate ratios for use in the process of the invention may be any flow rate ratio of the second flowing stream:first flowing stream as described herein. The flow rate ratio will be governed by the size of the crystals that are required for a given end purpose and the proposed delivery vehicle that may be used in a subject organism.

Typically, the flow rate of the non-solvent stream through an apparatus suitable for producing crystalline particles using the process of the invention is in the range of liters per hour (L/hr) [e.g. 20 L/hr] rather than milliliters per hour (ml/hr) and may be any flow rate suitable for the end purpose in question. For example, the flow rate of the non-solvent can be higher than that of the solvent (ie the solution) as herein described. For example, the flow rate for the first stream flow of the invention may be 20 L/hr and that of the second stream flow 60 ml/hr for a bench top apparatus. Where the process is employed in a larger apparatus, for example, a 100 liter (100 L) vessel the throughput flow rates for the first stream may be 2400 L/hr and for the second stream 120 L/hr. Naturally, the man skilled in the art will appreciate that the rate of flow for each of the said streams can be at any desired speed provided that the flow rate ratio of the two streams is that described for the present invention The flow rate of the non-solvent for a small scale apparatus, such as one having a 1 liter capacity, 5 liter or 10 liter capacity, may be up to 50 L/hr, typically up to 40 L/hr, 30 L/hr, 20 L/hr 10 L/hr or 5 L/hr or of any value in between, such as 4 L/hr, 8 L/hr, 15 L/hr and so on. The flow rate may be decided upon by the skilled addressee depending on the size of particles required for a chosen administration route to a site of interest for a particular end purpose. Correspondingly, the flow rate of the added solution of solute in solvent can be the same or less than that of the non-solvent, for example, at least 20 times less than that of the non-solvent with which it is to be placed in contact. An example of a flow rate ratio (1000:1) used in the present invention is to be found in the examples wherein the non-solvent flows at 20 L/hr and the solute in solvent at 20 ml/hr.

It will be appreciated that the non-solvent and the solvent should be selected as being suitable for a particular active principal or active precursor thereof. The non-solvent and solvent should show a degree of immiscibility with each other as described herein, and are preferably immiscible with each other. Typically, the non-solvent can comprise an aqueous component, such as water, saline (5% w/w), or Tween 80. Examples of non-solvent:solution immiscible pairs include water (non-solvent) and ibuprofen in solvent such as cetyl alcohol with acetone; saline solution (non-solvent) and fluticasone in solvent such as dichloromethane; and Tween 80 (non-solvent) and ibuprofen in solvent such as dichloromethane. The selection of appropriate solvent and non-solvent must be made in accordance with the substance to be crystallised.

Once inside the chamber or receptacle an emulsion is formed. The combined streams of non-solvent and solvent may be subjected to ultrasonic irradiation to form crystals of a desired mean size, for example, in a continuous ultrasonic flow cell. The ultrasonic energy induces nucleation and subsequent crystallisation of the solute in the non-solvent in the operating vicinity of the ultrasonic probe if used, or of an ultrasonic energy transducer, such as a wrap-around ultrasonic energy transducer, if such a configuration is employed. The ultrasonic energy may be applied continuously or in a discontinuous manner, such as by pulsed application. Any suitable source of ultrasonic irradiation may be used. An ultrasonic probe may, for example, be inserted into a mixing vessel, such as a continuous ultrasonic flow cell, an ultrasonic emitter may be contained in the mixing vessel, or the mixing vessel may be housed in an ultrasonic bath or it may have an ultrasound transducer fixed to the external walls of the mixing vessel. The amplitude and frequency of the ultrasound waves affects the rate of nucleation and crystal growth. The frequency of the ultrasound waves may for example be from 20 kHz to 1 MHz, preferably from 10-500 kHz, more preferably from 10-100 kHz such as at 10, at 20, 40, 60, 80, or 100 kHz or at any frequency thereinbetween, such as, 30 kHz or 50 kHz.

The ultrasonic irradiation is employed at an amplitude that is appropriate for the formation of crystals of the desired size, for a pre-determined application. For laboratory probe systems with an emitting face of, for example 80 $cm^2$, the amplitude selected may be from about 1-30 μm, typically from 3-20 μm, preferably from 5-10 μm, for example, 6 μm. Probes having a probe face surface area of 8 $cm^2$ and a power requirement of from 5-80 W, provide a power density of from 0.6-12.5 $W/cm^2$ using an amplitude of 2-15 μm. In larger systems, comprising transducers bonded onto the flow cell, for example a 6 liter flow cell, the power density for the transducers employed may be from 10-100 W/L, preferably from 30-80 W/L, and more preferably from 50-75 W/L, for example 60W/L or 70 W/L.

The residence time of the mixed components in the ultrasonic flow cell may be from 10 ms up to about 10 s. For re-circulation systems the residence time can be longer depending on design. The skilled addressee will appreciate that the residence time in the ultrasonic flow cell for each volume of fluid that is placed in it will be of the order of 10 ms up to 10 s, depending on design, The process may be employed in reactors employed in the art such as in a batch fed reactor or in a continuous flow reactor, depending on design. The man skilled in the art is well acquainted with such reactor types and their operation. Generated crystals may be gathered or harvested from the batch chamber by drawing off crystals using conventional means in the art, such as by the process described in WO 03/092851 or as an aqueous suspension.

DETAILED DESCRIPTION OF THE INVENTION

The invention will now be described with reference to the accompanying examples and figures. It is to be understood that the examples and figures are not to be construed as limiting the scope of the invention in any manner.

The process of the invention may be carried out using conventional equipment as shown in the accompanying figures in which:

FIG. 1 shows a longitudinal sectional view of a crystallisation apparatus incorporating two separate feed stream delivery means for the solvent and anti-solvent leading into an ultrasonic continuous flow cell having an ultrasonic probe placed therein;

FIG. 2 shows a longitudinal sectional view of a crystallisation apparatus incorporating a single feed stream delivery means where the solvent and anti-solvent are introduced coaxially, mixed, and driven in a single stream into an ultrasonic continuous flow cell having an ultrasonic transducing apparatus bonded onto it;

FIG. 3: size distribution of ibuprofen particles;

FIG. 4: size distribution of fluticasone propionate particles; and

FIG. 5: size distribution of ibuprofen-loaded particles of wax prepared from cetyl alcohol.

FIG. 6: size distribution of Budenoside nanoparticles by emulsion crystallisation.

FIG. 7: size distribution of Budenoside nanoparticles by emulsion crystallization.

Turning to FIG. 1, closed loop crystallisation apparatus 10 comprises an impeller 5 in a first feed chamber 4 (surrounded by a thermal jacket 3), with an axial outlet 6 through which liquid non-solvent flows into a delivery means 7 and is pumped at a first flow rate via pump 8 into an ultrasonic flow cell chamber 12. Concurrently, a supersaturated solution of liquid solute in solvent is pumped via a pump 9 at a flow rate different from that of the non-solvent from a second chamber (not shown) via delivery means 10 through to delivery means 11 and into ultrasonic flow cell chamber 12 where the two liquids are mixed. Ultrasonic probe 1 irradiates the mixture with ultrasonic energy and the mixture flows through an outlet 2 and into the first feed chamber 4, completing a continuous closed flow loop. The flow cycle is repeated until crystallised particles of a desired size are attained. Thus in use of the apparatus 10, the saturated solution is thoroughly and rapidly mixed with the non-solvent, the volume of the chamber 4 and the flow rates being such that the residence time in the ultrasonic flow cell chamber 12 is for example, 10 s. The ultrasonic energy from the probe 1 insonates the entire volume of the chamber 12 with sufficient intensity to cause dispersion and nucleation, as localised cavitation occurring on a microscopic scale promotes changes in fluid temperature and pressure that induce nucleation (and also promotes formation of the stable polymorph). By adjusting the power of the ultrasound, and the residence time in chamber 12, the degree of nucleation can therefore be controlled. The ultrasound has the additional benefit that any crystal deposits within the chamber 12 tend to be removed from the surfaces.

Figure 1:
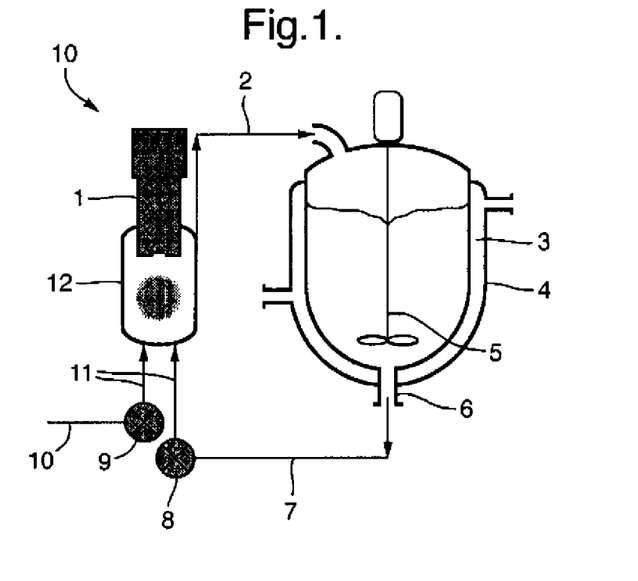

The skilled addressee will appreciate that the closed loop crystallisation apparatus 10 of FIG. 1 may be configured differently, for example, by replacing delivery means 11 with a single delivery means wherein the two liquid feeds from delivery means 7 and 10 may be contacted coaxially therein, prior to being fed into ultrasonic flow cell chamber 12 through a single inlet.

Figure 2:
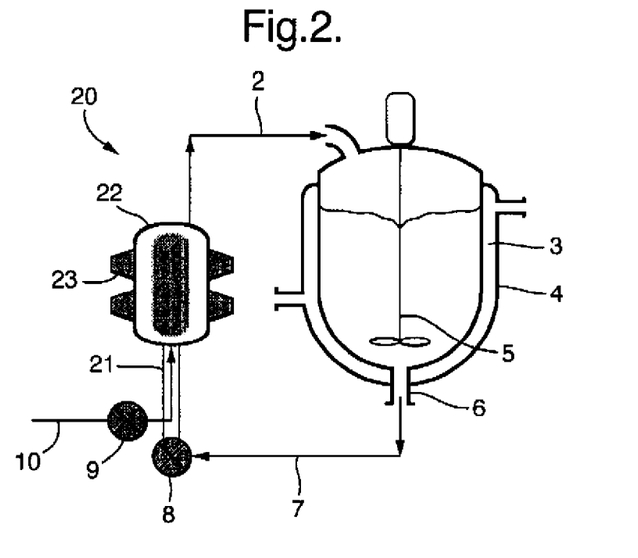

Referring to FIG. 2, closed loop crystallisation apparatus 20 is of a similar configuration to that of FIG. 1 except that chamber 22 has a wrap-around ultrasonic transducer 23 located on the external surface of it. The wrap-around transducer 23 insonates the entire volume of the chamber 23 with sufficient intensity to cause nucleation and by adjusting the power of the ultrasound, and the residence time in the chamber 23, the degree of nucleation can therefore be controlled. The ultrasound has the additional benefit that any crystal deposits within the chamber 23 tend to be removed from the surfaces.

A further difference of the configuration of FIG. 2 from that of FIG. 1 is that the two liquid feeds from delivery means 7 and 10 are contacted coaxially within a single delivery means 21 and fed into the ultrasonic chamber 22 via a single inlet.

The skilled addressee will again appreciate that the delivery means to the ultrasonic flow chamber 22 could also follow the configuration of that of FIG. 1.

The skilled addressee will appreciate that the thermal jacket is designed to help maintain the temperature of the non-solvent at a desired temperature, depending on design.

EXAMPLE 1

Ibuprofen Nanoparticles by Emulsion Crystallization and Evaporation

Water (800 mL) was charged to a 1 L stirred crystallizer fitted with a thermo-regulation jacket. The temperature was adjusted to 45° C. Water was pumped around a recirculation loop using a diaphragm pump (operating at 20 L/h) and a 250 ml thermo-regulated glass ultrasonic flow-cell fitted with a 30 mm diameter 20 kHz ultrasonic probe. The probe was held at the highest position in the flow-cell and sealed/clamped at a point of zero vibration (null point). The flow-cell was thermo-regulated at 45° C. Continuous ultrasound was applied at 15 W power, 5 micron amplitude. Ibuprofen (150 mg) was dissolved in dichloromethane (25 mL). The solution was dispersed in an aqueous phase held at 45° C. consisting of 800 ml of a 0.2% (w/v) solution of Tween 80. The dichloromethane solution was pumped into the ultrasonic flow-cell using a second inlet on the underside of the flow-cell at a rate of 20 ml/h. The resulting suspension was stirred for 30 minutes at 300 rpm with sonication. Product was collected as aqueous suspension. Particle size distribution is shown in FIG. 3.

EXAMPLE 2

Fluticasone Propionate Nanoparticles by Emulsion Crystallization and Evaporation Saline solution (0.5% w/w) was charged to a 1 L stirred crystallizer fitted with thermoregulation jacket. The temperature was adjusted to 45° C. Saline water was pumped around a recirculation loop using a diaphragm pump (operating at 20 L/h) and a 250 mL thermo-regulated glass ultrasonic flow-cell fitted with a 30 mm diameter 20 kHz ultrasonic probe. The probe was held at the highest position in the flow-cell and sealed/clamped at a point of zero vibration (null point). The flow-cell was thermo-regulated at 45° C. Continuous ultrasound was applied at 15 W power, 5 micron amplitude. Fluticasone propionate (0.5 g) was dissolved in dichloromethane (40 mL). The solution was dispersed in an aqueous phase held at 45° C. consisting of 800 mL of a 0.5% (w/w) saline solution. The dichloromethane solution was pumped into the ultrasonic flow-cell using a second inlet on the underside of the flow-cell at a rate of 20 mL/h. The resulting suspension was stirred for 30 minutes at 45° C. & 300 rpm under continuous sonication. Product was collected as aqueous suspension. Particle size distribution is shown in FIG. 4.

EXAMPLE 3

Ibuprofen-Loaded Nanoparticles of Wax Prepared from Cetyl Alcohol

Water (1 L) was charged to a 1 L stirred crystallizer fitted with thermoregulation jacket. The temperature was adjusted to 55° C. Water was pumped around a recirculation loop using a diaphragm pump (operating at 20 L/h) and a 60 mL thermo-regulated glass ultrasonic flow-cell fitted with a 30 mm diameter 20 kHz ultrasonic probe. The probe was held at the highest position in the flow-cell and sealed/clamped at a point of zero vibration (null point). The flow-cell was thermo-regulated at 55° C. Continuous ultrasound was applied at 15 W power, 5 μm amplitude. Ibuprofen (0.2 g) was co-dissolved with cetyl alcohol (2 g) in acetone (10 mL). The solution was dispersed in an aqueous phase consisting of 1 L of a 0.3% (w/v) solution of Tween 80. The acetone solution was pumped into the ultrasonic flow-cell using a second inlet on the underside of the flow-cell at a rate of 20 mL/h. The resulting dispersion was cooled to 5° C. (at the rate of −1° C./min) under continuous sonication. Product was collected as an aqueous suspension. Particle size distribution is as shown in FIG. 5.

EXAMPLE 4

Budenoside Nanoparticles by Emulsion Crystallisation

Heptane (0.75 L) was charged to a 1 L stirred crystallizer (250 rpm) fitted with a thermo-regulation jacket. The temperature was adjusted to 5° C. The water was pumped around a recirculation loop using a diaphragm pump (operating at 20 l/h) and a 60 ml thermo-regulated glass ultrasonic flow-cell fitted with a 30 mm diameter 20 kHz ultrasonic probe. The probe was held at the highest position in the flow-cell and sealed/clamped at a point of zero vibration (node point). The flow-cell was thermo-regulated at 5° C. Continuous ultrasound was applied at 15 W power, 5 micron amplitude. Budesonide (1.5 g) was dissolved in methanol (100 mL) and then pumped into the ultrasonic flow-cell using a second inlet on the underside of the flow-cell at a rate of 20 mL/h. Upon complete addition of the budesonide solution, the mixture was kept under recirculation for further 30 minutes. The microcrystalline product was isolated by either supercritical carbon dioxide assisted drying (to remove non-polar solvents), micro-filtration or spray drying. Particle size distribution is as shown in FIG. 6.

EXAMPLE 5

Budenoside Nanoparticles by Emulsion Crystallisation

Water (800 mL) was charged to a 1 L stirred crystallizer fitted with a thermo-regulation jacket. The temperature was adjusted to 45° C. Water was pumped around a recirculation loop using a diaphragm pump (operating at 20 L/h) and a 250 ml thermo-regulated glass ultrasonic flow-cell fitted with a 30 mm diameter 20 kHz ultrasonic probe. The probe was held at the highest position in the flow-cell and sealed/clamped at a point of zero vibration (null point). The flow-cell was thermo-regulated at 45° C. Continuous ultrasound was applied at 15 W power, 5 micron amplitude. Budesonide (0.8 g) was dissolved in dichloromethane (80 mL). The solution was dispersed in an aqueous phase held at 45° C. consisting of 800 ml of a 0.2% (w/v) solution of Tween 80. The dichloromethane solution was pumped into the ultrasonic flow-cell using a second inlet on the underside of the flow-cell at a rate of 20 ml/h. The resulting suspension was stirred for 30 minutes at 300 rpm with sonication. Product was collected as aqueous suspension.

Malvern laser defraction particle size analysis (Mastersizer 2000) showing particle size distribution is shown in FIG. 7.

What is claimed:

1. A process for preparing crystalline particles of at least one active principal and wherein a batch of liquid non-solvent with a pre-set volume is charged to an apparatus comprising a closed flow loop incorporating an ultrasonic flow cell, the process comprising:

(A) recirculating the batch of liquid non-solvent around the closed flow loop at a first flow rate;

(B) introducing a saturated solution of at least one solute in a solvent to the ultrasonic flow cell chamber at a second flow rate, wherein the flow rate ratio of the non-solvent: the saturated solution is at least 20:1;

(C) thereby contacting and mixing the liquid non-solvent with the saturated solution of at least one solute in the solvent in the ultrasonic flow cell chamber, wherein the non-solvent and the solvent are not miscible with each other forming an emulsion of droplets or dispersion of droplets;

(D) providing ultrasonic energy to the emulsion or the dispersion, the ultrasound irradiation inducing nucleation and so crystallization of the at least one solute;

(E) during introduction of the saturated solution, continuously recirculating the batch of liquid non-solvent, with the added at least one solute and the resultant crystalline particles, around the closed flow loop and through the ultrasonic flow cell, wherein the pre-set volume of the non-solvent and the flow rate of the non-solvent are selected such that, during introduction of the solution, the non-solvent is recirculated multiple times around the closed flow loop; and (F) subsequently isolating the resulting crystalline particles.

2. A process according to claim 1 wherein the solute is present in a super-saturated solution within droplets of the emulsion or the dispersion formed in step (C).

3. A process according to claim 2 wherein the super-saturation is achieved by cooling the solution in the droplets.

4. A process according to claim 1 wherein the recirculation around the closed flow loop is repeated until crystallized particles of a desired size are attained.

5. A process according to claim 1 wherein the ultrasonic energy is provided by an ultrasonic probe or a wrap-around ultrasonic transducer.

6. A process according to claim 2 wherein the solvent is volatile at the temperature of the non-solvent and evaporation of the solvent leads to super-saturation within the droplets.

7. A process according to claim 1 wherein the emulsion or dispersion comprises at least one active principal or a precursor thereof, and a carrier substance.

8. A process according to claim 1 wherein the emulsion or dispersion comprises a mixture of two active principals.

9. A process according to claim 1 wherein the active principal is selected from fluticasone and ibuprofen.

10. A process according to claim 1 wherein the emulsion or dispersion comprises an active principal or carrier substance.

* * * * *